(12) United States Patent
Brånemark et al.

(10) Patent No.: US 9,408,723 B2
(45) Date of Patent: Aug. 9, 2016

(54) CONNECTION DEVICE

(71) Applicant: Integrum AB, Mölndal (SE)

(72) Inventors: Rickard Brånemark, Mölndal (SE); Birger Roos, Järfalla (SE); Erik Ax, Hyggen (NO)

(73) Assignee: Integrum AB (SE)

( * ) Notice: Subject to any disclaimer, the term of this patent is extended or adjusted under 35 U.S.C. 154(b) by 30 days.

(21) Appl. No.: 14/384,440

(22) PCT Filed: Mar. 8, 2013

(86) PCT No.: PCT/SE2013/050205
§ 371 (c)(1),
(2) Date: Sep. 11, 2014

(87) PCT Pub. No.: WO2013/141777
PCT Pub. Date: Sep. 26, 2013

(65) Prior Publication Data
US 2015/0257904 A1    Sep. 17, 2015

(30) Foreign Application Priority Data
Mar. 19, 2012 (SE) ..................................... 1250256

(51) Int. Cl.
*A61F 2/78* (2006.01)
*A61F 2/50* (2006.01)
*A61F 2/76* (2006.01)

(52) U.S. Cl.
CPC ... *A61F 2/78* (2013.01); *A61F 2/76* (2013.01); *A61F 2002/503* (2013.01); *A61F 2002/5003* (2013.01); *A61F 2002/5016* (2013.01); *A61F 2002/5039* (2013.01); *A61F 2002/5043* (2013.01); *A61F 2002/5072* (2013.01); *A61F 2002/5083* (2013.01); *A61F 2002/7887* (2013.01)

(58) Field of Classification Search
CPC ...... A61F 2/76; A61F 2/78; A61F 2002/7887
See application file for complete search history.

(56) References Cited

U.S. PATENT DOCUMENTS 5,571,212 A * 11/1996 Cornelius ............. A61F 2/6607
                                                623/47
8,246,693 B2 * 8/2012 Bachus ................. A61F 2/2814
                                                623/32

(Continued)

FOREIGN PATENT DOCUMENTS

GB           2479532 A    10/2011
WO    WO-2007/018904 A2    2/2007
WO    WO 2011/094602 A1    8/2011

OTHER PUBLICATIONS

European Patent Office Extended Search Report for EP Application No. 13764339.1, dated Oct. 23, 2015, 6 pages.

*Primary Examiner* — Marcia Watkins
(74) *Attorney, Agent, or Firm* — Foley & Lardner LLP

(57) ABSTRACT

The invention relates to a connection device for connecting an implant system anchored in bone with an external prosthesis component, such as a limb prosthesis, prosthetic knee elbow or finger. The connection device includes a main housing, a first attachment portion arranged for attachment to the implant system and a second attachment portion arranged for attachment to the prosthesis component. It further includes a safety mechanism to protect the implant system from high mechanical forces, including rotational forces and or bending forces. According to one aspect of the invention the safety mechanism includes a rotational force release mechanism. This includes a first component including a ring unit having an inner surface with at least one depression and a second component includes at least one plunge unit urged into contact with said the depression by said spring means. According to another aspect the safety mechanism includes a bending force release mechanism with the second attachment portion being pivotable and having a spring loaded cam unit acting on a cam surface of the main hosing. According to a further aspect the safety mechanism is arranged to limit rotating forces as well as bending forces.

19 Claims, 2 Drawing Sheets

(56) References Cited

U.S. PATENT DOCUMENTS

Figure 1:
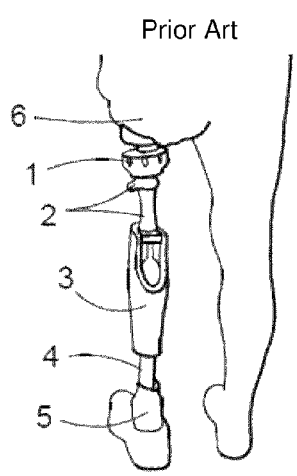

| | | | |
|---|---|---|---|
| 2008/0161938 A1* | 7/2008 | Gramnas | A61F 2/76 623/33 |
| 2008/0288087 A1 | 11/2008 | Bachus et al. | |
| 2012/0310371 A1* | 12/2012 | Bachus | A61F 2/76 623/32 |
| 2013/0195540 A1* | 8/2013 | Wozencroft | A61F 2/78 403/83 |

* cited by examiner

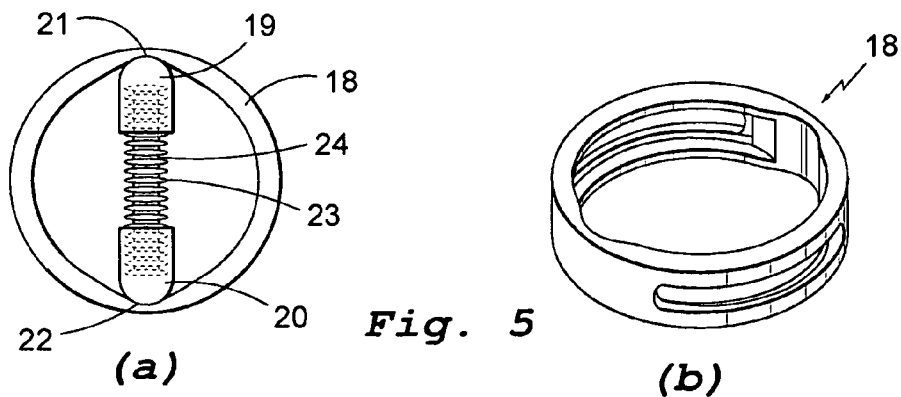
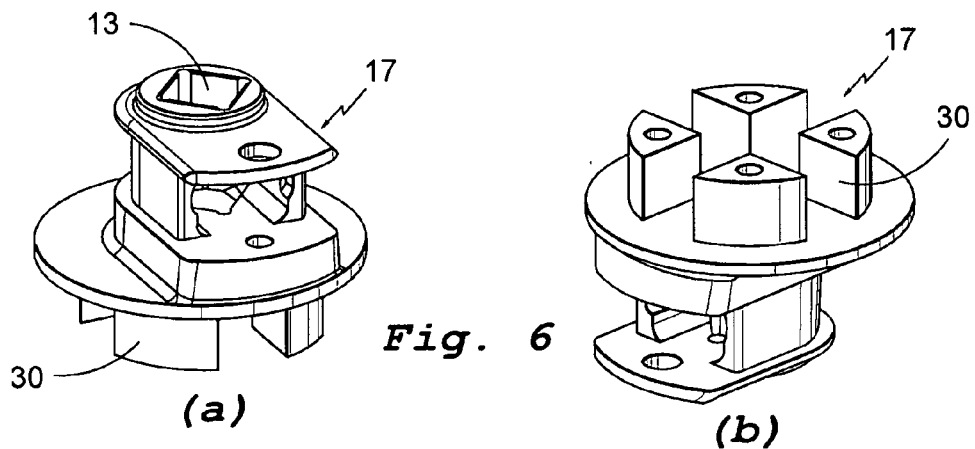
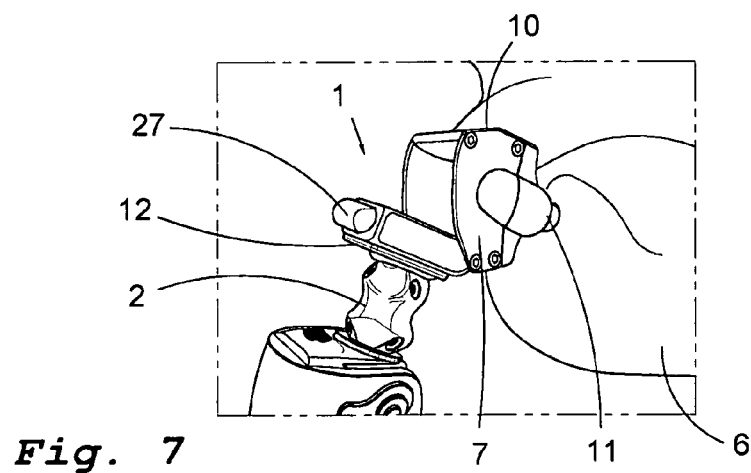
Fig. 5
Fig. 6
Fig. 7

CONNECTION DEVICE

FIELD OF INVENTION

The present invention relates to a device for connecting an osseointegrated implant system to an external prosthetic component, such as a limb prosthesis or prosthetic knee. The connection device is designed to protect the implant system from high mechanical forces and to avoid any skeletal fracture caused by an accident situation. The function is to limit rotational forces in the centre line of the implant and/or bending forces when the prosthetic component (prosthetic knee or elbow for example) is natural bent to its maximum position.

BACKGROUND OF INVENTION

Osseointegrated prostheses for rehabilitation of amputees (OPRA system) have been developed and commercialized by Integrum AB, Mölndal, Sweden. The OPRA system is currently used to anchor limb prostheses by means of a titanium implant that is surgically inserted into the bone. Generally, the OPRA system consists of a titanium screw implanted inside the bone and which serves as a fixture for the abutment, an abutment which is partly inserted inside the fixture and partly exiting the bone and stump so that the attachment of the artificial limb can be arranged at the head of the abutment, and an abutment screw for attaching the abutment to the fixture thus providing the mechanical coupling between the fixture and the abutment.

The connection device is arranged at the top of the prosthesis and forms the attachment between the abutment and the prosthesis. Specifically, it allows the attachment of the prosthetic component distal to the abutment. Also, the connector has a built-in safety mechanism to prevent bone damage in the event of excessive loads such as in a fall or other overload. All amputees are likely to have overloads or fall occasionally and a complication following osseointegration is the risk of bending the abutment. If the abutment is bent or deformed following a fall, then it must be replaced. And if the anchoring of the fixture is disturbed then there is a risk of loosening the fixture and a there has to be a new surgical operation.

In the event of unfavourable rotational loads being applied to the implant system it is previously known (see OPRA ROTASAFE system, also developed and commercialized by Integrum AB, Mölndal, Sweden) to design the built-in safety mechanism with two separate torque plates that are arranged to rotate relative to each another when the rotational load exceeds a release level. The amount of torque required to activate the connector device can be adjusted and graded to the status of the patient. The torsion release level of the connector device should be set to protect the implant system from significant rotational overload but still allow everyday activities without frequent release episodes that will disturb the patient and could increase wearing of the device. For instance the release level of the connector device could be altered between 10 Nm and 30 Nm, for instance by means of a number of press screws.

However, there is a need to reduce the outer dimensions of the connector device and also makes it more easy to set the release level instead of using as much as 8 press screws for controlling the release level.

There is also a need to take care of excessive bending forces, because in the event of an accidental fall not only rotational overload but also such unfavourable bending forces might occur. Even if it has been proposed to design a connector device with a release function for such excessive bending torques, there has been no success so far.

SUMMARY OF INVENTION

It is an object of the present invention to provide a connector device having a built-in mechanism to limit bending forces and which can be built-in to a connector device having a more compact design compared to previous solutions.

It is a further object to provide a connector device where the built in mechanism also is able to limit rotational forces.

It is also an object of the invention to provide a connector device having a more simple system for controlling the release level.

It is a further object of the invention to provide a connector device having a quick connection to the abutment and which is more easy to operate.

According to the invention the connector device has a main housing which includes a built-in safety mechanism to protect the implant system from high mechanical forces and to avoid any skeletal fracture caused by an overload situation and wherein the built-in safety mechanism is arranged to limit bending forces.

According to a preferred embodiment the built-in safety mechanism comprises a first release mechanism to prevent also rotating forces to be translated from the prosthetics in to the bone itself as well as the mechanism to limit bending forces when the prosthetic knee is natural bent to its maximum position, for instance in case the patient has a backwards fall and ends up sitting on the prosthetics, and then will secure the implant or bone itself from damage.

According to a further embodiment the first release mechanism is arranged in the upper part of the housing (facing the implant system) and the second release mechanism is arranged in the lower part of the main housing (facing the external prosthetic device).

According to a further embodiment the connector device has an excenter arm for quick connection and locking of the connector device to the abutment of the implant system.

Further preferred embodiments of the invention are specified in the dependent claims. It is to be understood that still further preferred embodiments can be constituted by any possible combination of the features in the claims, the above mentioned features and by features related to the description of an example.

By the term rotational force in the present application is meant a torque force around an axis defined by the axis of an anchoring screw of the implant system or around an axis in parallel thereto or slightly angled thereto. By the term bending force is ment a force perpendicular to this axis.

SHORT DESCRIPTION OF THE FIGURES

Figure 2:
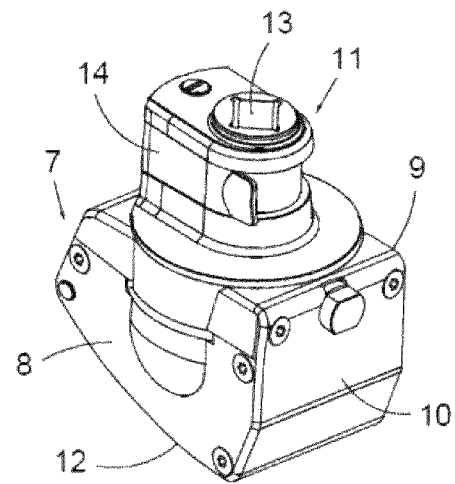
Figure 3:
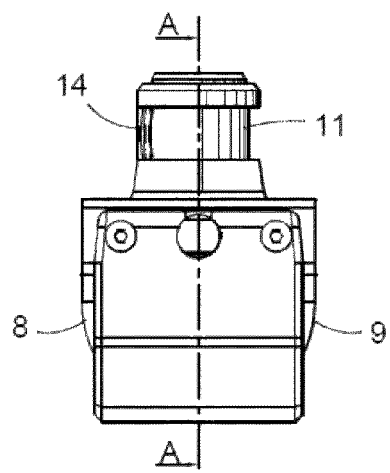
Figure 4:
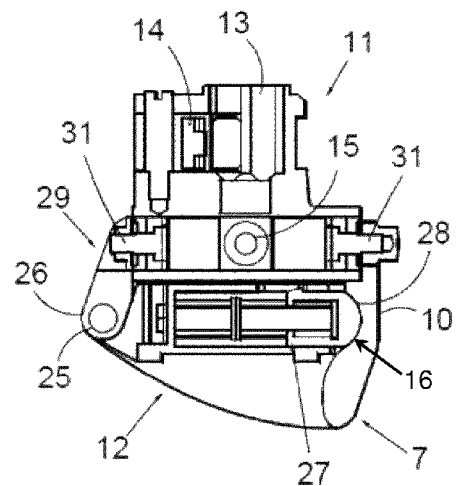

In the following an example of the invention will be described more in detail with reference to the accompanying drawings, in which FIG. 1 is an overview of an osseointegrated prior art prosthesis for rehabilitation of amputees, FIG. 2 is a schematic view of a connection device according to the invention, FIG. 3 is a side view of the connection device, FIG. 4 is a section through the connection device along A-A in FIG. 3, FIGS. 5*a* and 5*b* illustrates the main parts of the release mechanism for rotational overload, FIGS. 6*a* and 6*b* illustrates the main fitting cooperating with the rotational release mechanism, and FIG. 7 illustrates the release mechanism for excessive bending torques in open released position.

DESCRIPTION OF EXAMPLE

In FIG. 1 it is illustrated the different components of an osseointegrated implant system for rehabilitation of amputees. In this case the external prosthetics comprises a connection device 1, distance and optional adapters 2, knee prosthesis 3, further distance and optional adapters 4 and a foot prosthesis 5. The external prosthetic device is anchored to the bone stump 6 by means of a titanium implant that is surgically inserted into the bone. It is completely implanted inside the bone and osseointegrated and serves as a fixture for a skin penetrating connection, the abutment. The abutment component is attached to the fixture and partly exiting the bone and stump. The artificial limb, i e the external prosthetic device, is then attached at the head of the abutment.

Bone anchored prostheses of this type which are based on osseointegration allow a direct connection of an artificial limb prosthesis to the patient's skeleton, thus avoiding the use of a socket. Osseointegrated prostheses for rehabilitation of amputees (OPRA system) have been developed and commercialized by Integrum AB, Mölndal, Sweden, and will not be described in any further detail here.

As mentioned in the introductory part of the specification all amputees are likely to fall occasionally and a complication following osseointegration is the risk of bending the abutment or jeopardizing the anchoring of the osseointegrated fixture due to high mechanical forces. If the abutment is bent or deformed following a fall, then it must be replaced. If the anchoring of the fixture is disturbed then there is a risk of loosening of the fixture and a new surgical operation might be required.

In the event of unfavourable rotational loads being applied to the implant system it is previously known to design the connection device 1 with a built-in safety mechanism designed to protect the implant system from high mechanical forces, specifically rotational loads, in order to avoid any skeletal fracture caused by an accident situation. The built-in safety mechanism has a release function which is activated when a rotational load exceeds a pre-set release level.

As illustrated in FIG. 1 the connection device 1 forms the interface between the implant system and the prosthetic device. The connection device is arranged at the top of the prosthesis and forms the attachment between the abutment and the prosthesis. Specifically, it allows the attachment of the prosthetic component distal to the abutment. According to the invention, the connection device has a new built-in safety mechanism to reduce accidental high mechanical forces on the implant system, in the event of for instance a fall. As illustrated in FIG. 2 the connection device has a main housing 7 with right and left side portions 8, 9 and an end portion 10. The main housing 7 includes the safety mechanism which will be described more in detail below. The connection device also has an upper protruding part 11 for connection to an abutment portion of the implant system and a lower prosthetic attachment portion 12 for connection to the prosthesis component. The upper protruding part has a non-circular opening or recess 13 for securing the abutment portion and an excenter shaft mechanism with a squeezer operated by a mechanical lever 14 for a quick locking and release of the abutment in the recess hole 13.

FIG. 3 is a front end view of the connection device illustrating the outside of the main housing 7 and upper protruding part 11 for the abutment connection.

FIG. 4 is a section through line A-A in FIG. 3 illustrating the built-in safety mechanism. The built-in safety mechanism comprises a rotational force release mechanism 15 to prevent rotating forces to be translated from the prosthetics in to the bone itself. This rotational force release mechanism is arranged in the upper part of the main housing. The built-in safety mechanism also comprises a bending force release mechanism 16 to limit bending forces when the prosthetic knee is naturally bent to its maximum position, for instance in case the patient has a backwards fall and ends up sitting on the prosthetics, and then will secure the implant or bone itself from damage. This bending force release mechanism is arranged in the lower part of the main housing.

The function of the rotational force release mechanism 15 is to limit rotational forces in the centre line of the implant. In the event of excessive torque being applied to the system, the components that form the body of the connection device are arranged to rotate relative to each another. The amount of torque required to release the mechanism can be adjusted and graded to the status of the patient. The torsion release level of the connection device should be set to protect the implant system from significant rotational overload but still allow everyday activities without frequent release episodes that will disturb the patient and could increase wearing of the device Specifically, the components that form the rotational force release mechanism 15 includes a main fitting 17 as illustrated in FIG. 6a (top view) and FIG. 6b (bottom view). The main fitting has a four-leg geometry cooperating with an inner ring arrangement to provide a relative movement between the main fitting 17 and the inner ring 18, which is illustrated in FIGS. 5a and 5b. In normal use the two parts are in a fixed rotational position relative to each other by means of two spring actuated torque punches 19, 20 cooperating with two diametrically opposed rounded notches 21, 22 in the inner wall of the inner ring 18. A number of disc springs 23 are arranged around a longitudinal peg 24 to provide a desired torque release level. For instance the release level of the connector device could be altered between 10 Nm and 30 Nm, by changing the number of disc springs at factory. For instance factory setting of the torque release level could be 15 Nm. When released, the prosthetic leg/foot can be freely rotated around the implant axis. The torque resets automatically when the foot goes to the normal position. The pair of punches 19, 20 with its spring packet are located in the interspace between pairs of legs 30 to transmit torque to the main fitting 17 of the attachment portion connected to the implant system.

The two movable parts are initially set in a fixed rotational position relative to each other by means of at least one rotation adjustment screw 31 in order to lock the prosthetic foot in its natural position relative to the implant system. After the connection device has been connected to the implant abutment and the excenter arm 14 has been locked, the rotation adjustment screws 31 are opened. The prosthetic foot is adjusted according to the abutment position and the rotation adjustment screws are tightened to lock the position of the prosthetic foot.

The function of the bending force release mechanism 16 is to limit bending forces when the prosthetic knee is naturally bent. This function is achieved by arranging the lower prosthetic attachment portion 12 to swing from a closed, unreleased and natural position as in FIGS. 2 and 4 to an open released position as illustrated in FIG. 7. Specifically, the attachment portion is pivotably arranged on a pivot shaft 25 supported in a bending bracket 26 arranged on one side 29 of the lower part of the main housing. The attachment portion includes a spring actuated punch member forming a cam unit 27 cooperating with a rounded groove 28 formed on the inner wall of the end portion 10 of the main housing opposite to the side where the pivot pin 25 is mounted. The groove 28 forms a cam surface that has a curved profile downwards in the figure. The cam unit 27 has a longitudinal extension parallel to the pivot shaft 25 as shown in FIG. 7 when the mechanism has released. A moderate downward bending force on the attachment unit will not be sufficient to move the cam unit out of contact with the groove 28. For a higher bending force this force will be sufficient to press the cam unit 27 to the left in the figure whilst travelling downwards along the cam surface and allow the attachment device to be released to the position in FIG. 7. The factory setting of the bend release could be set to 70 Nm. After release the mechanism is easily reset by closing the prosthetic attachment portion 12 again, just by pushing the hand on it.

It should be understood that the bending force release mechanism is arranged to limit bending forces in the same plane as the natural bending of the prosthetic knee. This is achieved by the orientation of the bending shaft 25 which is locked in its position by means of said rotation adjustment screws.

The invention claimed is:

1. A connection device for connecting an implant system anchored in bone with an external prosthesis component, the connection device comprising:
   a main housing,
   a first attachment portion arranged for attachment to the implant system,
   a second attachment portion arranged for attachment to the prosthesis component, and
   a safety mechanism to protect the implant system from high mechanical forces, the safety mechanism including a bending force release mechanism, the bending force release mechanism including a pivot pin arranged in said main housing, wherein the pivot pin defines a pivot axis, wherein the second attachment portion is mounted pivotable around said pivot axis, wherein the second attachment portion includes a spring-loaded cam unit acting on a cam surface on the main hosing, wherein the spring loaded cam unit is pivotable around said pivot axis, and wherein the bending force release mechanism operates solely for bending forces around said pivot axis.

2. A connection device according to claim 1, wherein the prosthesis component is for a joint having a joint axis and the orientation of the pivot pin is such that it is in parallel with the joint axis.

3. A connection device according to claim 2, wherein the first attachment portion includes a non-circular hole for receiving a part of the implant system, wherein the hole defines a center axis, said center axis being substantially perpendicular to said pivot axis and being located at a certain distance from the pivot axis, wherein said certain distance is determined for a certain bending force.

4. A connection device according to claim 2, wherein the safety mechanism is arranged to limit rotating forces as well as bending forces, and comprises a rotational force release mechanism to prevent rotating forces to be translated from the external prosthesis component to the bone.

5. A connection device according to claim 2, wherein the device includes an abutment coupling part comprising an excenter arm for quick connection and locking of the connection device to an abutment of the implant system.

6. A connection device according to claim 1, wherein the first attachment portion includes a non-circular hole for receiving a part of the implant system, wherein the hole defines a center axis, said center axis being substantially perpendicular to said pivot axis and being located at a certain distance from the pivot axis, wherein said certain distance is determined for a certain bending force.

7. A connection device according to claim 6, wherein the device includes an abutment coupling part comprising an excenter arm for quick connection and locking of the connection device to an abutment of the implant system.

8. A connection device according to claim 6, wherein the safety mechanism is arranged to limit rotating forces as well as bending forces, and comprises a rotational force release mechanism to prevent rotating forces to be translated from the external prosthesis component to the bone.

9. A connection device according to claim 1, wherein the safety mechanism is arranged to limit rotating forces as well as bending forces, and comprises a rotational force release mechanism to prevent rotating forces to be translated from the external prosthesis component to the bone.

10. A connection device according to claim 9, wherein the rotational force release mechanism comprises a plurality of components arranged to rotate relative to one another in an event of excessive torque being applied to the implant system.

11. A connection device according to claim 9, wherein the device includes an abutment coupling part comprising an excenter arm for quick connection and locking of the connection device to an abutment of the implant system.

12. A connection device according to claim 10, wherein the rotational force release mechanism includes a first component connected to one of said first attachment portion or said main housing, a second component connected to the other of said first attachment portion or main housing, the first component including a ring unit having an inner surface with at least one depression, the second component including plunger means and spring means, wherein the plunger means has at least one plunger unit wherein the at least one plunger unit is urged into contact with said at least one depression by said spring means.

13. A connection device according to claim 10, wherein the device includes an abutment coupling part comprising an excenter arm for quick connection and locking of the connection device to an abutment of the implant system.

14. A connection device according to claim 12, wherein said first component is connected to said main housing, and said second component is connected to said first attachment portion.

15. A connection device according to claim 12, wherein the inner surface of the ring unit has two depressions diametrically opposed to each other and the plunger means has two oppositely directed plunger units contacting a respective one of said depressions and the spring means is arranged to urge the plunger units away from each other.

16. A connection device according to claim 12, wherein the rotational force release mechanism is arranged with relation to the first attachment portion.

17. A connection device according to claim 12, wherein the device includes an abutment coupling part comprising an excenter arm for quick connection and locking of the connection device to an abutment of the implant system.

18. A connection device according to claim 1, wherein the device includes an abutment coupling part comprising an excenter arm for quick connection and locking of the connection device to an abutment of the implant system.

19. A connection device according to claim 1, wherein the bending force release mechanism is arranged with relation to the second attachment portion.

* * * * *